United States Patent
Mai

[11] Patent Number: 5,246,443
[45] Date of Patent: Sep. 21, 1993

[54] CLIP AND OSTEOSYNTHESIS PLATE WITH DYNAMIC COMPRESSION AND SELF-RETENTION

[76] Inventor: Christian Mai, 74 boulevard des Belges, 69006 Lyon, France

[21] Appl. No.: 875,226

[22] Filed: Apr. 28, 1992

[51] Int. Cl.⁵ .............................................. A61B 17/00
[52] U.S. Cl. ........................................ 606/78; 606/72; 606/219
[58] Field of Search ................... 606/78, 72, 219, 220, 606/222, 138

[56] References Cited

U.S. PATENT DOCUMENTS

| | | |
|---|---|---|
| 3,786,806 | 1/1974 | Johnson et al. |
| 4,170,990 | 10/1979 | Baumgart et al. |
| 4,454,875 | 6/1984 | Pratt et al. |
| 4,485,816 | 12/1984 | Krumme. |
| 5,002,563 | 3/1991 | Pyka et al. ........................... 606/222 |
| 5,067,957 | 11/1991 | Jervis ................................. 606/108 |

FOREIGN PATENT DOCUMENTS

| | | |
|---|---|---|
| 1149106 | 5/1983 | Canada. |
| 0145166 | 6/1985 | European Pat. Off. |
| 2703529 | 3/1978 | Fed. Rep. of Germany. |
| 8305106 | 3/1983 | France. |
| 940759 | 7/1982 | U.S.S.R. |

OTHER PUBLICATIONS

G. Bensmann, et al. 294 Techn. Mitt. Krupp, vol. 37 No. 1 (1979-06).
Flexmedics Corporation; Nitinol . . . The Material of Choice for Safer More Effective Medical Procedures; (Product Literature).

Primary Examiner—Stephen C. Pellegrino
Assistant Examiner—Gary Jackson
Attorney, Agent, or Firm—Wall and Roehrig

[57] ABSTRACT

Osteosynthesis plate, made of a thermoelastic martensitic alloy whose transformation temperatures are:
martensitic transformation temperature Ms below 10° C.;
austenitic transformation temperature As above 15° C.,
the cross-over from the martensitic temperature to the austenitic temperature bringing about a shortening of the length of the plate, characterized in that it is educated to take a rectilinear shape at a temperature below the martensitic transformation temperature Ms of the material of which the plate is made, and an undulated shape at a temperature above the austenitic transformation temperature as of the said material.

15 Claims, 3 Drawing Sheets

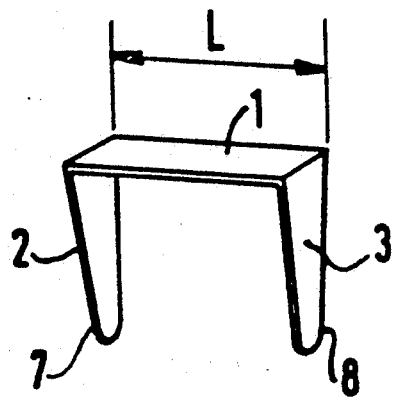
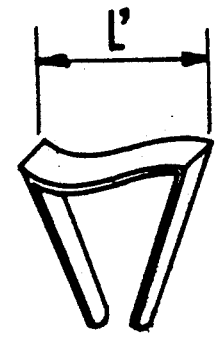
FIG.1     FIG.2
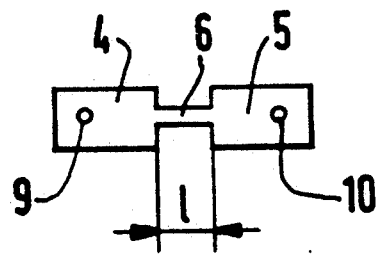
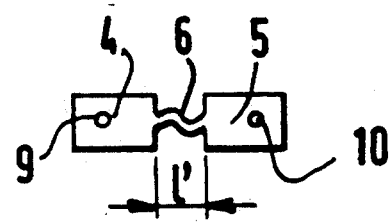
FIG.3     FIG.4
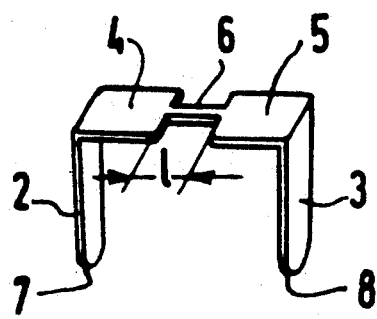
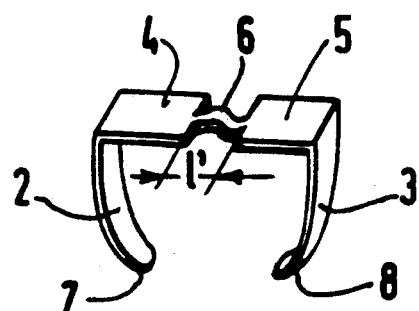
FIG.5     FIG.6

CLIP AND OSTEOSYNTHESIS PLATE WITH DYNAMIC COMPRESSION AND SELF-RETENTION

BACKGROUND OF THE INVENTION

The invention relates to a new type of clip and osteosynthesis plate having characteristics of dynamic compression and self-retention.

The term "dynamic compression" signifies the ability of these clips or plates to generate a compression force resulting between the two points at the level of which they are implanted and, more particularly, on each side of a bone fracture area.

The surgical clips used for the fixation of the bones and soft tissues must possess a number of essential characteristics. First, they must develop a compression which is constant over time. In addition, they must be anchored perfectly in such a way as to prevent unhooking after their implantation, this unhooking generally being due to movements of the articulation or simply of the bone on which they are implanted. Finally, the method of implantation or removal of the clips and plates must be simple, easy to implement, and cause a minimum level of osseous traumatism.

Various types of clips or plates aimed at achieving these aims are currently known. For example, in order to ensure their retention in the soft bone, clips have been proposed whose lateral branches are equipped with projecting parts or ridges, which are intended to prevent the withdrawal of the clip from the tissue (FR-A-2,525,102). However, although it is true that this type of clip eliminates any risk of unloosening from the bone to be fixed, it does not generate any dynamic compression and, in addition, the removal of the clip results in considerable osseous traumatism.

It has also been proposed, particularly in the document DE-A-2,703,529, to produce clips made of martensitic material (of alloy of the Ni—Ti or Ti—Nb type), and to confer upon the branches of the clips a shape memory capable of inducing a moving together of their ends above the austenitic temperature of the said martensitic material of which the clip is made. This "shape memory" phenomenon is due to the reversible thermoelastic martensitic transformation. This phenomenon is well known and consists in giving to a material a defined shape which is treated at a temperature above the austenitic temperature As of the material, then in giving it another shape, likewise defined, at a temperature below the martensitic temperature Ms of the said material, and finally in repeating this operation several times as a function of the nature of the alloy used, in order to give this material its definitive shape memory. This temperature Ms is below the temperature As.

However, although it is true that this type of clip provides a dynamic compression at the level of the end of the clips, this dynamic compression generally proves inadequate for the whole of the fracture at the level of which the clip is implanted, and is even in some cases damaging because this compression is asymmetrical; indeed, it brings together the deeper areas of the fracture zone and distances the superficial area of this same zone.

SUMMARY OF THE INVENTION

The invention aims to overcome these various disadvantages. It concerns a clip or an osteosynthesis plate capable of satisfying the various criteria set out hereinabove and able to generate a global dynamic compression at the level of the actual fracture on which the clip or the plate is implemented, and additionally having qualities of self-retention.

This osteosynthesis plate is made of a thermoelastic martensitic alloy whose transformation temperatures are:

martensitic transformation temperature Ms below 10° C.;

austenitic transformation temperature As above 15° C., the cross-over from the martensitic temperature to the austenitic temperature bringing about a shortening of the length of the plate.

It is characterised in that it is educated to take a rectilinear shape at a temperature below the martensitic transformation temperature Ms and an undulated shape at a temperature above the austenitic transformation temperature As.

The invention also relates to an osteosynthesis clip having two branches intended to be inserted on each side of the area of the bone fracture to be repaired, the said branches being educated so as to deform and in particular move together under the effect of the temperature, above the austenitic transformation temperature As, the said branches being connected via a connection base, which consists of a plate of the type previously mentioned.

Thus, when the clip assembly is at a temperature greater than or equal to the austenitic transformation temperature, not only do the ends of the clips move together, but in addition, and in particular, the connection base itself shortens, inducing at the level of the fracture on which it is implanted a dynamic compression both at the level of the spongy bone and at the level of the cortical bone, or at the level of both the upper and lower parts of the cortical bone when the clip passes right through the bone.

Advantageously, in practice:
the clip is a monobloc clip;
the branches are mounted on the connection base;
only a portion of the connection base is educated;
the portion of the base which is reduced and educated has a cross-section smaller than the total cross-section of the base;
the plate or the connection base has at least two continuous openings situated in the vicinity of their end, and intended to permit the said plate or base to be fixed by any suitable means, and in particular by screws;
the free ends of the lateral branches of the clip are also educated to increase their surface in the general plane containing them at a temperature above the austenitic temperature;
one of the lateral branches consists of at least three sections, a first and a third section, respectively, these sections being educated so as to be on the whole perpendicular to the connection base at a temperature below the martensitic temperature, the first section, adjoining the said base, being educated to move away from the other lateral branch at a temperature above the austenitic temperature, and the third section being educated, in contrast, to move towards the other lateral branch at a temperature above the austenitic temperature, the said first and third sections being in addition connected via a second section which is on the whole parallel to the connection base;
the free end of the third section is split longitudinally, the two zones thus defined being educated so as to remain parallel and in alignment with the said third section at a temperature below the martensitic temperature, and to move apart in the plane of the said section at a temperature above the austenitic temperature;

the clip is made up of two clips of the type in question, joined together in the vicinity of the middle of their connection base, these clips being educated on each side of this joining zone, or on one side only;

the clip comprises three branches, in a Y shape, the connection bases of the said branches in the joining zone, or only some of them, being educated in accordance with the invention;

the alloy of the clip is an alloy based on titanium/nickel or a copper/aluminium/zinc alloy.

BRIEF DESCRIPTION OF THE DRAWINGS

The manner in which the invention can be implemented and the advantages which derive therefrom will emerge more clearly from the exemplary embodiments which follow and which are given by way of indication and as non-limiting examples, with reference to the attached figures, in which:

FIG. 1 is a diagrammatic view of the clip according to the invention at a temperature below the martensitic transformation temperature;

FIG. 2 is a view similar to that in FIG. 1 at a temperature above the austenitic transformation temperature;

FIG. 3 is a view of an osteosynthesis plate according to the invention at a temperature below the martensitic transformation temperature;

FIG. 4 is a view similar to that in FIG. 3 at a temperature above the austenitic transformation temperature;

FIG. 5 is a view of another embodiment of the clip, at a temperature below the martensitic temperature;

FIG. 6 is a view similar to that in FIG. 5, at a temperature above the austenitic temperature;

DETAILED DESCRIPTION OF A PREFERRED EMBODIMENT

Figure 7:
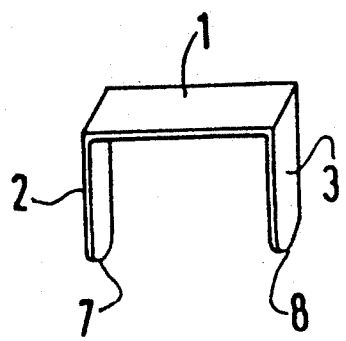
FIG. 7 is a representation of another embodiment of the clip, at a temperature below the martensitic temperature.

An osteosynthesis clip essentially consists of a base (1) on which the two lateral branches (2,3) are mounted. These lateral branches (2,3) are smooth, or granular, and can be slightly tapered at their free end (7,8) in order to facilitate their insertion during implantation of the clip, at the martensitic temperature, in the bone tissues of the fracture. In a known manner, and in accordance with the particular therapeutic applications, the length of the branches (2,3) can be identical or different. Moreover, the branches can be perpendicular or inclined relative to the connection base.

According to an essential characteristic of the invention, the clip is made of a thermoelastic martensitic material satisfying the necessary criteria of biocompatibility. This martensitic material typically consists of a nickel/titanium alloy or an alloy based on copper, aluminium and zinc.

The martensitic temperature Ms of the material is typically in the region of 10° C. At this temperature, the lateral branches (2,3) on the one hand and the connection base (1) on the other hand undergo repeated deformations in order to induce a shape-memory effect, which will be restored when the austenitic temperature threshold, i.e. typically 25° C., is exceeded. This shape memory can be acquired by the various elements, namely lateral branches and connection base, by giving them a particular shape at a temperature above the austenitic transformation temperature As, then by giving them another shape, and in particular a straight shape, at a temperature below the martensitic transformation temperature. By repeating these mechanical transformations a certain number of times, a rectilinear shape memory, respectively for the connection base and the lateral branches, at a temperature below the martensitic temperature, and an undulated shape memory, such as that shown in FIG. 2, for the connection base, with the lateral branches moving together at a temperature above the austenitic threshold, are obtained.

In a particular embodiment, the clip is monobloc. However, in another embodiment, it is possible for the lateral branches (2,3) to be mounted., by any known means, on the connection base (1).

In an embodiment shown in FIGS. 5 and 6, the connection base consists of three parts, namely two end parts (4,5) of given profile, and an intermediate part (6) of smaller cross-section, joining these two parts. In this way, it is therefore possible to give a shape memory solely to this intermediate part, an undulated shape memory such as that shown in FIG. 6. This undulation of the intermediate section (6) can be effected in the general plane of the connection base (1), as shown in FIG. 6, or in another plane, and in particular in a plane perpendicular to the general plane of the said base (1). This undulation of the intermediate section (6) brings about a shortening of the connection base (1) of the clip, and consequently a dynamic compression of the fracture at this level. It will be noted in FIGS. 3, 4, 5 and 6 that the length L of the joining section (6), when it is rectilinear, that is to say at a temperature below the martensitic transformation temperature Ms, is reduced to the length $L'<l$ at a temperature above the austenitic transformation temperature. This reduction results in the reduction of the overall length L of the connection base to a value $L'<L$, this reduction having a typical value in the region of one and a half millimeters (1.5 mm).

When the connection base (1) attains a certain length, it may be necessary to connect it to the bone to be repaired. This connection is carried out by means of screws which are inserted into the bone through continuous openings (9,10) formed in the connection base in the vicinity of its ends (see FIGS. 3-6).

In other words, the clip according to the invention makes it possible to obtain a double compression effect, namely both at the intramedullary level, by way of the lateral branches (2,3) whose ends (7,8) move together, and at the outer level at the very surface of the bone, in the region of the cortical bone. In addition, given the deformation of the ends of the lateral branches of the clip, the latter is self-retaining.

For its positioning, the clip assembly is brought to a temperature below the martensitic transformation temperature. At this temperature, the connection base (1) and the two lateral branches (2,3) are rendered rectilinear, the said branches being on the whole perpendicular to the connection base (1). The clip is then implanted in the rectilinear position on each side of the fracture area, and this is done by means of compaction, preliminary holes having been made beforehand by the surgeon. Since the temperature of the human body is above the austenitic temperature, the clip deforms and adopts a shape defined by the shape memory already acquired. A shortening of the connection base is observed on the one hand and, on the other hand, a moving together of the free ends (7,8) of its lateral branches (2,3), this leading not only to the double compression effect already mentioned, but also to a self-retention of the clip.

Thus, as long as the temperature of the clip remains above the austenitic temperature, the clip remains firmly implanted in the bone. In order to remove the clip, it suffices to cool the clip to a temperature below the martensitic transformation temperature, and this is done by any suitable means. It is thus possible to remove the clip gently, without any risk of causing osseous traumatism.

In FIGS. 3 and 4, an osteosynthesis plate has been shown which is of a type entirely similar to the connection base hereinabove. This plate comprises, in particular, continuous openings (9,10) intended to permit its fixation, by means of screws, on the bone to be repaired. As in the preceding case, at a temperature above the austenitic temperature the intermediate section is reduced from a length L to a length L'<l, thus bringing about a dynamic compression in the bone to be repaired.

Figure 8:
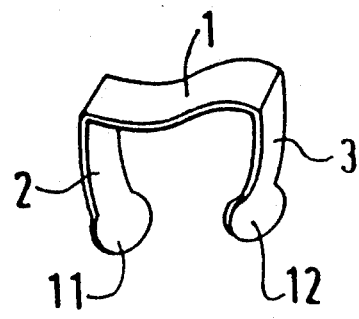
FIG. 8 is a view similar to that in FIG. 7, at a temperature above the austenitic temperature.

In an embodiment illustrated more particularly in FIGS. 7 and 8, the free end (7,8) of each of the lateral branches of the clip is educated so as to increase its surface in the plane containing each of the said branches (FIG. 8), at a temperature above the austenitic temperature. This is due to the fact that when under the martensitic transformation temperature the lateral branches are longer than they are when above the austenitic transformation temperature. When above the austentitic transformation temperature the connection base is educated to take on an undulating shape and thus the branches are closer together. This reduction in length when above the austenitic temperature induces, by shape memory effect, a corresponding increase in the planar surfaces of the lateral branches. This widening (11,12) thus makes it possible to increase the bearing surface of the said ends at the level of the spongy bone, and thereby to improve the "internal" dynamic compression in the bone to be repaired.

Figure 9:
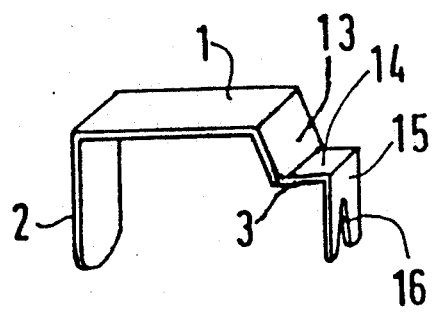
FIG. 9 is a representation of another embodiment of the clip, at a temperature below the martensitic temperature.
Figure 10:
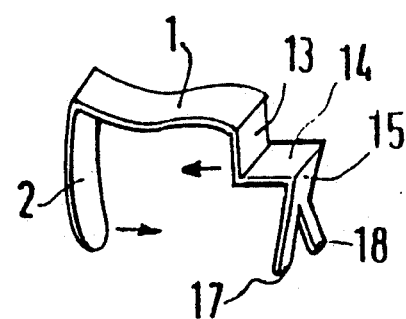
FIG. 10 is a view similar to that in FIG. 9, at a temperature above the austenitic temperature.

In another embodiment described in conjunction with FIGS. 9 and 10 and more especially adapted to the knee, one of the lateral branches (3) consists of three sections (13,14,15), each of them being rectilinear at a temperature below the martensitic transformation temperature. At such a temperature, the first section (13) is slightly distanced, by education, from the vertical, by a value in the region of 15 degrees. In contrast, the direction of the third section (15) is on the whole perpendicular to the connection base (1) of the clip. They are connected to one another via a second section (14) which is essentially parallel to the said base (1). In addition, the third section (15) has at its end a longitudinal slot (16) extending over a few millimetres, typically ten millimetres.

The first section (13) receives a shape-memory education which is such that, at a temperature above the austenitic temperature, it moves towards the other lateral branch (2) and becomes on the whole perpendicular to the connection base (1), this resulting, consequently, in the other sections (14,15) moving closer to the said branch (2).

The third section (15) also receives a shapememory education, and this at two levels. First, at a temperature above the austenitic temperature the said third section (15) moves towards the lateral branch (2), and this in order to bring about a dynamic compression effect similar to that described in the preceding examples. Finally, at such a temperature, the two zones (17,18) defined by the slot (16) at the level of the end (8) of this section move apart from one another in the plane of the said section (15), in order to bring about a retention effect at this level.

It is also possible, in this embodiment, to provide continuous openings (not shown) on the connection base (1), on the one hand, and on the second section (14) of the lateral branch, on the other hand, in order to permit a more substantial fixation of the clip on its implantation site.

Figure 11:
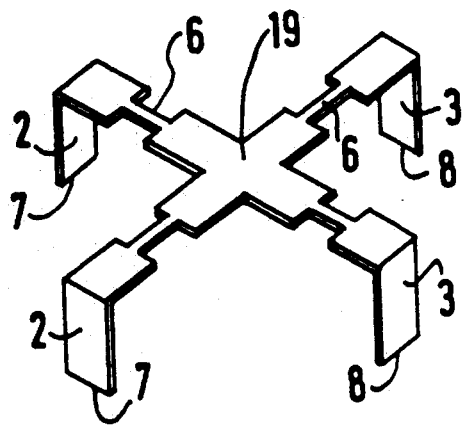
FIG. 11 is a diagrammatic representation of another embodiment of the clip, at a temperature below the martensitic temperature.
Figure 12:
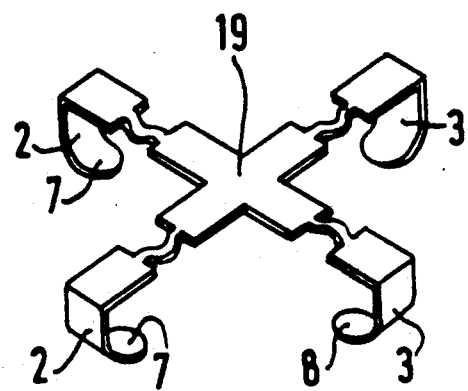
FIG. 12 is a view similar to that in FIG. 11, at a temperature above the austenitic temperature.

In another embodiment described more particularly in FIGS. 11 and 12, the clip has the shape of an X and is in fact made up of two clips of a type previously described, joined together, for example by welding, in the vicinity of the middle (19) of their connection base. In this particular case, the said connection bases (1) are educated to take an undulated shape at a temperature above the austenitic transformation temperature As of the material from which they are made. More specifically, and in an advantageous embodiment, the said connection bases each comprise two intermediate parts (6) of smaller cross-section, positioned on each side of the joining zone of the two clips. In this way, the resulting clip proves especially suitable for the reduction of a complicated fracture.

Figure 13:
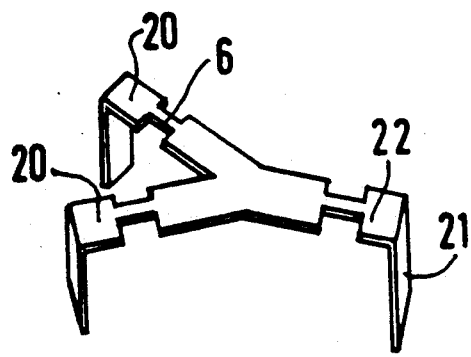
FIG. 13 is a diagrammatic representation of another embodiment of the clip, at a temperature below the martensitic temperature.
Figure 14:
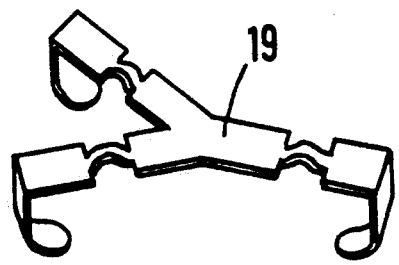
FIG. 14 is a view similar to that in FIG. 13, at a temperature above the austenitic temperature.

Similarly, the embodiment shown in FIGS. 13 and 14 concerns a complex clip having the shape of a Y. The three branches (20) of the Y are joined together, for example by welding. However, it is conceivable that this particular structure could be obtained by folding a simple clip whose two original ends are educated to curve inwards at a temperature above the austenitic transformation temperature of the material, as for the clips described above, and whose folding zone (21), constituting the end of the base branch (22) of the Y, is also educated to adopt this particular profile.

In addition, it is conceivable that each of the branches could comprise an intermediate portion of smaller cross-section (6), as described above, or that only some of them could be provided with such a cross-section, educated to adopt an undulated shape at a temperature above the austenitic transformation temperature of the material from which they are made, in such a way as to induce a shortening of the branch in question. Thus, it is possible to select the most suitable structure depending on the particular application of the clip.

The osteosynthesis plates and clips according to the invention prove perfectly adapted to the roles which are assigned to them, particularly for generating a double dynamic compression effect at the level of the bone fractures.

I claim:

1. An osteosynthesis plate, made of a thermoelastic martensitic alloy whose martensitic transformation temperature is below 10° C., and whose austenitic transformation temperature is above 15° C.;

wherein crossing over from the martensitic to the austenitic temperature results in a shortening of the length of the plate;

wherein the plate is educated to take a rectilinear shape at temperatures below the martensitic transformation temperature of the alloy from which said plate is fabricated and an undulated shape at temperatures above the austenitic transformation temperature of said alloy; and wherein only a portion of said plate is educated and the educated portion of said plate is at all times of a cross-section smaller than the overall cross-section of said plate.

2. An osteosynthesis plate according to claim 1 having an opening in the vicinity of each of its end, said opening allowing connection of the plate by means of screws to a bone to be repaired.

3. An osteosynthesis plate, having a length, fabricated of a thermoelastic martensitic alloy having a martensitic transformation temperature below 10° C., and an austenitic transformation temperature above 15° C.;

wherein crossing over from the martensitic transformation temperature to the austenitic transformation temperature results in a shortening of the length of the plate;

wherein the plate is educated to take a rectilinear shape at temperatures below the martensitic transformation temperature of the alloy from which said plate is fabricated and an undulated shape at temperatures above the austenitic transformation temperature of said alloy; and wherein only a portion of said plate is educated and the educated portion of said plate is at all times of a cross-section smaller than the overall cross-section of said plate.

4. An osteosynthesis plate according to claim 3, having two ends, and having an opening proximate to of each of said ends, said opening allowing connection of the plate by means of screws to a bone to be repaired.

5. An osteosynthesis plate, according to claim 3, which is self-retaining and demonstrates global dynamic compression at both a spongy bone and cortical bone level.

6. An osteosynthesis clip, fabricated of a thermoelastic martensitic alloy having a martensitic transformation temperature below 10° C., and an austenitic transformation temperature above 15° C., comprising:

1) a connection base plate, having two ends and a length, wherein crossing over from the martensitic transformation temperature to the austenitic transformation temperature results in a shortening of the length of the connection base plate; and wherein the connection base plate is educated to take a rectilinear shape at temperatures below the martensitic transformation temperature of the alloy from which said connection base plate is fabricated and an undulated shape at temperatures above the austenitic transformation temperature of said alloy; and 2) a first branch and a second branch, each branch having one free end and a planar surface, and each branch being connected to one end of said base plate, said branches being intended to be inserted with one branch on each side of an area of a bone fracture to be repaired, said branches being educated so as to deform and move when brought to a temperature above the austenitic transformation temperature of the alloy from which the clip is fabricated.

7. An osteosynthesis clip according to claim 6 which is formed as a monobloc (a single piece of metal).

8. An osteosynthesis clip according to claim 7 wherein the branches are attached to the connection base plate.

9. An osteosynthesis clip according to claim 6 wherein the free end of each branch is educated so as to increase the planar surface of the free end of said branch when at a temperature above the austenitic transformation temperature of the alloy from which the clip is fabricated.

10. An osteosynthesis clip according to claim 6 wherein the first branch comprises at least three sections, being, respectively:

a first section adjoining the connection base plate and educated to move away from the second branch at temperatures below the martensitic transformation temperature and to move toward said second branch at temperatures above the austenitic transformation temperature;

a third section, having a free end, said third section being educated so as to be perpendicular to the connection base plate at temperatures below the martensitic transformation temperature, and so that said third section moves away from the second branch at temperatures above the austenitic transformation temperature; and a second section parallel to the connection base plate, said second section connecting the first and third sections.

11. An osteosynthesis clip according to claim 10 wherein the third section occupies a plane, and the free end of the third section of the first branch is split longitudinally, defining two zones, the two zones thus defined being educated to remain parallel to and in alignment with said third section of said first branch at temperatures below the martensitic transformation temperature, and to move apart from one another in the plane of the third section at temperatures above the austenitic transformation temperature.

12. An osteosynthesis clip comprised of two sub-clips, each according to claim 6, the connection base plate of each of said sub-clips having a middle, and said sub-clips being joined together in the vicinity of the middle of the connection bases of said sub-clips to form an "X" shape, wherein all of said branches are oriented in a common direction.

13. An osteosynthesis clip according to claim 12 wherein each of the two sub-clips at all times has a reduced cross section on either side of the join of said sub-clip to the other sub-clip, and said reduced cross section is educated to adopt an undulated shape at temperatures above the austenitic transformation temperature of the alloy from which said clip is fabricated.

14. An osteosynthesis clip according to claim 12 wherein only one of the two sub-clips has at all times a reduced cross section on either side of the join of said sub-clip to the other sub-clip and said reduced cross section is educated to adopt an undulated shape at temperatures above the austenitic transformation temperature of the alloy from which said clip is fabricated.

15. An osteosynthesis clip, fabricated of a thermoelastic martensitic alloy having a martensitic transformation temperature below 10° C., and an austenitic transformation temperature above 15° C., comprising:
1) a "Y" shaped connection base plate, comprising a first branch, a second branch, and a third branch, all said branches being in a single plane, each branch having a length and a free end, wherein crossing over from the martensitic transformation temperature to the austenitic transformation temperature results in a shortening of the length of at least one branch of the connection base plate; and wherein at least one branch of the connection base plate is educated to take a rectilinear shape at temperatures below the martensitic transformation temperature of the alloy from which said connection base plate is fabricated and an undulated shape at temperatures above the austenitic transformation temperature of said alloy; said branch having
2) a first and a second segment, each segment being connected to the free end of one branch, said clip being intended to be inserted with the segments of the first branch on one side of an area of a bone fracture to be repaired and the segments of the second and third branches on the other side of an area of a bone fracture to be repaired, said segments being educated so as to deform and move under the effect of temperature above the austenitic transformation temperature.

* * * * *